US012196856B2

United States Patent
Alspaugh et al.

(10) Patent No.: US 12,196,856 B2
(45) Date of Patent: Jan. 14, 2025

(54) ALIGNMENT SYSTEMS AND METHODS

(71) Applicant: Wright Medical Technology, Inc., Memphis, TN (US)

(72) Inventors: Julia C. Alspaugh, Memphis, TN (US); David G. Reynolds, Fairport, NY (US)

(73) Assignee: WRIGHT MEDICAL TECHNOLOGY, Memphis, TN (US)

( * ) Notice: Subject to any disclaimer, the term of this patent is extended or adjusted under 35 U.S.C. 154(b) by 302 days.

(21) Appl. No.: 17/661,196

(22) Filed: Apr. 28, 2022

(65) Prior Publication Data

US 2022/0397670 A1 Dec. 15, 2022

Related U.S. Application Data

(60) Provisional application No. 63/208,572, filed on Jun. 9, 2021.

(51) Int. Cl.
| | |
|---|---|
| *G01S 17/46* | (2006.01) |
| *A61B 6/12* | (2006.01) |
| *A61B 17/00* | (2006.01) |
| *A61B 90/00* | (2016.01) |
| *G01S 5/16* | (2006.01) |

(52) U.S. Cl.
CPC ............ *G01S 17/46* (2013.01); *A61B 6/12* (2013.01); *G01S 5/166* (2013.01); *A61B 2017/00725* (2013.01); *A61B 2090/3966* (2016.02)

(58) Field of Classification Search
CPC . G01S 17/46; G01S 5/166; A61B 6/12; A61B 2017/00725
See application file for complete search history.

(56) References Cited

U.S. PATENT DOCUMENTS

| 3,839,742 A | 10/1974 | Link |
| 3,872,519 A | 3/1975 | Giannestras et al. |

(Continued)

FOREIGN PATENT DOCUMENTS

| CA | 2836651 | 3/2016 |
| DE | 19501069 A1 | 7/1996 |

(Continued)

OTHER PUBLICATIONS

Anonymous: "Angle bracket (fastener)—Wikipedia", May 22, 2021, 1 page.

(Continued)

*Primary Examiner* — Edmond C Lau
*Assistant Examiner* — Joshua M Carlson
(74) *Attorney, Agent, or Firm* — DUANE MORRIS LLP

(57) ABSTRACT

Alignment systems and methods are disclosed. A system includes a first component and a second component. The first component has a first body supporting a first alignment member. The second component has a second body supporting a second alignment member. The first and second alignment members are separated from another and are configured to provide an indication that a fluoroscopic device is properly aligned with an anatomical plane when viewed under fluoroscopy. A method includes placing a first component supporting a first alignment member and a second component supporting a second alignment member relative to a patent, and aligning a fluoroscopic device with an anatomical plane using the first and second alignment members.

34 Claims, 9 Drawing Sheets

(56) References Cited

U.S. PATENT DOCUMENTS

| | | | |
|---|---|---|---|
| 3,886,599 A | 6/1975 | Schlein |
| 3,889,300 A | 6/1975 | Smith |
| 3,896,502 A | 7/1975 | Lennox |
| 3,896,503 A | 7/1975 | Freeman et al. |
| 3,975,778 A | 8/1976 | Newton, III |
| 3,987,500 A | 10/1976 | Schlein |
| 4,021,864 A | 5/1977 | Waugh |
| 4,069,518 A | 1/1978 | Groth, Jr. et al. |
| 4,156,944 A | 6/1979 | Schreiber et al. |
| 4,166,292 A | 9/1979 | Bokros |
| 4,204,284 A | 5/1980 | Koeneman |
| 4,232,404 A | 11/1980 | Samuelson et al. |
| 4,309,778 A | 1/1982 | Buechel et al. |
| 4,470,158 A | 9/1984 | Pappas et al. |
| 4,578,806 A | 3/1986 | Grass et al. |
| 4,755,185 A | 7/1988 | Tarr |
| 4,968,316 A | 11/1990 | Hergenroeder |
| 5,041,139 A | 8/1991 | Brånemark |
| 5,312,412 A | 5/1994 | Whipple |
| 5,326,365 A | 7/1994 | Alvine |
| 5,354,300 A | 10/1994 | Goble et al. |
| 5,423,825 A | 6/1995 | Levine |
| 5,476,466 A | 12/1995 | Barrette et al. |
| 5,601,563 A | 2/1997 | Burke et al. |
| 5,628,749 A | 5/1997 | Vendrely et al. |
| 5,634,927 A | 6/1997 | Houston et al. |
| 5,667,511 A | 9/1997 | Vendrely et al. |
| 5,674,223 A | 10/1997 | Cipolletti et al. |
| 5,735,904 A | 4/1998 | Pappas |
| 5,766,259 A | 6/1998 | Sammarco |
| 5,776,200 A | 7/1998 | Johnson et al. |
| 5,782,842 A | 7/1998 | Kloess et al. |
| 5,817,097 A | 10/1998 | Howard et al. |
| 5,824,106 A | 10/1998 | Fournal |
| 5,879,389 A | 3/1999 | Koshino |
| 5,885,299 A | 3/1999 | Winslow et al. |
| 5,888,203 A | 3/1999 | Goldberg |
| 5,897,559 A | 4/1999 | Masini |
| 5,935,132 A | 8/1999 | Bettuchi et al. |
| 6,002,859 A | 12/1999 | DiGioia, III et al. |
| 6,033,405 A | 3/2000 | Winslow et al. |
| 6,102,952 A | 8/2000 | Koshino |
| 6,183,519 B1 | 2/2001 | Bonnin et al. |
| 6,245,109 B1 | 6/2001 | Mendes et al. |
| 6,342,056 B1 | 1/2002 | Mac-Thiong et al. |
| 6,344,043 B1 | 2/2002 | Pappas |
| 6,409,767 B1 | 6/2002 | Perieéet al. |
| 6,436,146 B1 | 8/2002 | Hassler et al. |
| 6,478,800 B1 | 11/2002 | Fraser et al. |
| 6,520,964 B2 | 2/2003 | Tallarida et al. |
| 6,530,930 B1 | 3/2003 | Marino et al. |
| 6,610,067 B2 | 8/2003 | Tallarida et al. |
| 6,610,095 B1 | 8/2003 | Pope et al. |
| 6,620,168 B1 | 9/2003 | Lombardo et al. |
| 6,645,215 B1 | 11/2003 | McGovern et al. |
| 6,663,669 B1 | 12/2003 | Reiley |
| 6,673,116 B2 | 1/2004 | Reiley |
| 6,679,917 B2 | 1/2004 | Ek |
| 6,719,799 B1 | 4/2004 | Kropf |
| 6,824,567 B2 | 11/2004 | Tornier et al. |
| 6,852,130 B2 | 2/2005 | Keller et al. |
| 6,860,902 B2 | 3/2005 | Reiley |
| 6,863,691 B2 | 3/2005 | Short et al. |
| 6,875,222 B2 | 4/2005 | Long et al. |
| 6,875,236 B2 | 4/2005 | Reiley |
| 6,926,739 B1 | 8/2005 | O'Connor et al. |
| 6,939,380 B2 | 9/2005 | Guzman |
| 6,942,670 B2 | 9/2005 | Heldreth et al. |
| 7,001,394 B2 | 2/2006 | Gundlapalli et al. |
| 7,011,687 B2 | 3/2006 | Deffenbaugh et al. |
| 7,025,790 B2 | 4/2006 | Parks et al. |
| 7,163,541 B2 | 1/2007 | Ek |
| 7,238,190 B2 | 7/2007 | Schon et al. |
| 7,252,684 B2 | 8/2007 | Dearnaley |
| 7,314,488 B2 | 1/2008 | Reiley |
| 7,323,012 B1 | 1/2008 | Stone et al. |
| 7,476,227 B2 | 1/2009 | Tornier et al. |
| 7,481,814 B1 | 1/2009 | Metzger |
| 7,485,147 B2 | 2/2009 | Papps et al. |
| 7,534,246 B2 | 5/2009 | Reiley et al. |
| 7,534,270 B2 | 5/2009 | Ball |
| 7,615,082 B2 | 11/2009 | Naegerl et al. |
| 7,618,421 B2 | 11/2009 | Axelson, Jr. et al. |
| 7,625,409 B2 | 12/2009 | Saltzman et al. |
| 7,641,697 B2 | 1/2010 | Reiley |
| 7,678,151 B2 | 3/2010 | Ek |
| 7,713,305 B2 | 5/2010 | Ek |
| 7,717,920 B2 | 5/2010 | Reiley |
| 7,763,080 B2 | 7/2010 | Southworth |
| 7,794,144 B2 * | 9/2010 | Windt ............... A61B 6/4035 |
| | | 378/207 |
| 7,803,158 B2 | 9/2010 | Hayden |
| 7,850,698 B2 | 12/2010 | Straszheim-Morley et al. |
| 7,896,883 B2 | 3/2011 | Ek et al. |
| 7,896,885 B2 | 3/2011 | Miniaci et al. |
| 7,909,882 B2 | 3/2011 | Stinnette |
| 7,963,996 B2 | 6/2011 | Saltzman et al. |
| 8,002,841 B2 | 8/2011 | Hasselman |
| 8,012,217 B2 | 9/2011 | Strzepa et al. |
| 8,034,114 B2 | 10/2011 | Reiley |
| 8,034,115 B2 | 10/2011 | Reiley |
| 8,048,164 B2 | 11/2011 | Reiley |
| 8,083,746 B2 * | 12/2011 | Novak ............... A61B 17/8866 |
| | | 606/88 |
| 8,110,006 B2 | 2/2012 | Reiley |
| 8,114,091 B2 | 2/2012 | Ratron et al. |
| 8,167,888 B2 | 5/2012 | Steffensmeier |
| 8,172,850 B2 | 5/2012 | McMinn |
| 8,177,841 B2 | 5/2012 | Ek |
| 8,268,007 B2 | 9/2012 | Barsoum et al. |
| 8,303,667 B2 | 11/2012 | Younger |
| 8,313,492 B2 | 11/2012 | Wong et al. |
| 8,317,797 B2 | 11/2012 | Rasmussen |
| 8,323,346 B2 | 12/2012 | Tepic |
| 8,337,503 B2 | 12/2012 | Lian |
| 8,361,159 B2 | 1/2013 | Ek |
| 8,475,463 B2 | 7/2013 | Lian |
| 8,491,596 B2 | 7/2013 | Long et al. |
| 8,808,303 B2 | 8/2014 | Stemniski et al. |
| 8,911,444 B2 | 12/2014 | Bailey |
| 9,566,075 B2 | 2/2017 | Carroll et al. |
| 9,672,607 B2 | 6/2017 | Demri et al. |
| 9,901,353 B2 | 2/2018 | Carroll et al. |
| 9,907,561 B2 | 3/2018 | Luna et al. |
| 10,034,678 B2 | 7/2018 | Park et al. |
| 10,039,558 B2 | 8/2018 | Park et al. |
| 10,206,688 B2 | 2/2019 | Park et al. |
| 10,433,911 B2 | 10/2019 | Wang et al. |
| 10,722,200 B2 * | 7/2020 | Kiraly ............... A61B 6/466 |
| 2001/0053204 A1 * | 12/2001 | Navab ............... A61B 6/547 |
| | | 378/207 |
| 2002/0068977 A1 | 6/2002 | Jackson |
| 2002/0082607 A1 | 6/2002 | Heldreth et al. |
| 2002/0133164 A1 | 9/2002 | Williamson |
| 2002/0173853 A1 | 11/2002 | Corl, III et al. |
| 2003/0208280 A1 | 11/2003 | Tohidi |
| 2003/0236522 A1 | 12/2003 | Long et al. |
| 2004/0030399 A1 | 2/2004 | Asencio |
| 2004/0039394 A1 | 2/2004 | Conti et al. |
| 2004/0068322 A1 | 4/2004 | Ferree |
| 2004/0167631 A1 | 8/2004 | Luchesi et al. |
| 2004/0186585 A1 | 9/2004 | Feiwell |
| 2004/0216259 A1 | 11/2004 | Ponziani |
| 2004/0236431 A1 | 11/2004 | Sekel |
| 2005/0004676 A1 | 1/2005 | Schon et al. |
| 2005/0165408 A1 | 7/2005 | Puno et al. |
| 2005/0192674 A1 | 9/2005 | Ferree |
| 2006/0009857 A1 | 1/2006 | Gibbs et al. |
| 2006/0020345 A1 | 1/2006 | O'Connor et al. |
| 2006/0036257 A1 | 2/2006 | Steffensmeier |
| 2006/0116679 A1 | 6/2006 | Lutz et al. |
| 2006/0142870 A1 | 6/2006 | Robinson et al. |
| 2006/0235541 A1 | 10/2006 | Hodorek |
| 2006/0247788 A1 | 11/2006 | Ross |

(56) References Cited

U.S. PATENT DOCUMENTS

| | | |
|---|---|---|
| 2007/0038303 A1 | 2/2007 | Myerson et al. |
| 2007/0100346 A1 | 5/2007 | Wyss et al. |
| 2007/0112431 A1 | 5/2007 | Kofoed |
| 2007/0162025 A1 | 7/2007 | Tornier et al. |
| 2007/0173944 A1 | 7/2007 | Keller et al. |
| 2007/0173947 A1 | 7/2007 | Ratron |
| 2007/0203455 A1 | 8/2007 | Tremaglio, Jr. et al. |
| 2007/0213830 A1 | 9/2007 | Ammann et al. |
| 2007/0233129 A1 | 10/2007 | Bertagnoli et al. |
| 2007/0276400 A1 | 11/2007 | Moore et al. |
| 2007/0288030 A1 | 12/2007 | Metzger et al. |
| 2008/0015602 A1 | 1/2008 | Axelson |
| 2008/0097617 A1 | 4/2008 | Fellinger et al. |
| 2008/0103603 A1 | 5/2008 | Hintermann |
| 2008/0109081 A1 | 5/2008 | Bao et al. |
| 2008/0195233 A1 | 8/2008 | Ferrari et al. |
| 2008/0215156 A1 | 9/2008 | Duggal et al. |
| 2008/0287954 A1 | 11/2008 | Kunz et al. |
| 2008/0312745 A1 | 12/2008 | Keller et al. |
| 2009/0024131 A1 | 1/2009 | Metzger et al. |
| 2009/0043310 A1 | 2/2009 | Rasmussen |
| 2009/0054992 A1 | 2/2009 | Landes et al. |
| 2009/0082875 A1 | 3/2009 | Long |
| 2009/0105767 A1 | 4/2009 | Reiley |
| 2009/0105840 A1 | 4/2009 | Reiley |
| 2009/0182433 A1 | 7/2009 | Reiley et al. |
| 2009/0198341 A1 | 8/2009 | Choi et al. |
| 2009/0234360 A1 | 9/2009 | Alexander |
| 2009/0276052 A1 | 11/2009 | Regala et al. |
| 2010/0010493 A1 | 1/2010 | Dower |
| 2010/0023066 A1 | 1/2010 | Long et al. |
| 2010/0023126 A1 | 1/2010 | Grotz |
| 2010/0057216 A1 | 3/2010 | Gannoe et al. |
| 2010/0069910 A1 | 3/2010 | Hasselman |
| 2010/0198355 A1 | 8/2010 | Kofoed et al. |
| 2010/0241237 A1 | 9/2010 | Pappas |
| 2010/0305572 A1 | 12/2010 | Saltzman et al. |
| 2010/0318088 A1 | 12/2010 | Warne et al. |
| 2010/0331984 A1 | 12/2010 | Barsoum et al. |
| 2011/0029090 A1 | 2/2011 | Zannis et al. |
| 2011/0035018 A1 | 2/2011 | Deffenbaugh et al. |
| 2011/0035019 A1 | 2/2011 | Goswami et al. |
| 2011/0106268 A1 | 5/2011 | Deffenbaugh et al. |
| 2011/0125200 A1 | 5/2011 | Hanson et al. |
| 2011/0125275 A1 | 5/2011 | Lipman et al. |
| 2011/0125284 A1 | 5/2011 | Gabbrielli et al. |
| 2011/0152868 A1 | 6/2011 | Kourtis et al. |
| 2011/0152869 A1 | 6/2011 | Ek et al. |
| 2011/0166608 A1 | 7/2011 | Duggal et al. |
| 2011/0190829 A1 | 8/2011 | Duggal et al. |
| 2011/0218542 A1 | 9/2011 | Lian |
| 2011/0249793 A1* | 10/2011 | Lalena ................. A61B 6/4266 378/62 |
| 2011/0253151 A1 | 10/2011 | Tochigi et al. |
| 2011/0276052 A1 | 11/2011 | Hasselman |
| 2011/0295380 A1 | 12/2011 | Long |
| 2012/0010718 A1 | 1/2012 | Still |
| 2012/0046753 A1 | 2/2012 | Cook et al. |
| 2012/0053644 A1 | 3/2012 | Landry et al. |
| 2012/0083789 A1 | 4/2012 | Blakemore et al. |
| 2012/0109131 A1 | 5/2012 | Vasarhelyi et al. |
| 2012/0109326 A1 | 5/2012 | Perler |
| 2012/0130376 A1 | 5/2012 | Loring et al. |
| 2012/0136443 A1 | 5/2012 | Wenzel |
| 2012/0185057 A1 | 7/2012 | Abidi et al. |
| 2012/0191210 A1 | 7/2012 | Ratron et al. |
| 2012/0239045 A1 | 9/2012 | Li |
| 2012/0245701 A1 | 9/2012 | Zak et al. |
| 2012/0271430 A1 | 10/2012 | Arnett et al. |
| 2012/0277745 A1 | 11/2012 | Lizee |
| 2013/0041473 A1 | 2/2013 | Rouyer et al. |
| 2013/0116797 A1 | 5/2013 | Coulange et al. |
| 2014/0275955 A1 | 9/2014 | Crawford et al. |
| 2016/0135815 A1 | 5/2016 | Loring et al. |
| 2019/0209080 A1 | 7/2019 | Gullotti et al. |
| 2021/0405378 A1* | 12/2021 | Choi ...................... G02F 1/137 |

FOREIGN PATENT DOCUMENTS

| | | |
|---|---|---|
| EP | 2967697 | 4/2018 |
| EP | 3607898 B1 | 8/2021 |
| GB | 2480846 | 12/2011 |
| JP | H11-500035 | 1/1999 |
| JP | 2006150055 | 6/2006 |
| JP | 2007518453 | 7/2007 |
| JP | 2007519477 | 7/2007 |
| JP | 2007536011 | 12/2007 |
| JP | 2011526189 | 10/2011 |
| JP | 2012518517 | 8/2012 |
| JP | 2013500810 | 1/2013 |
| JP | 2013511358 | 4/2013 |
| JP | 2014131738 | 7/2014 |
| WO | WO 9625106 | 8/1996 |
| WO | WO 0166021 A1 | 9/2001 |
| WO | WO 2005011523 A2 | 2/2005 |
| WO | WO 2006022923 | 3/2006 |
| WO | WO 2006023824 | 3/2006 |
| WO | WO 2006099270 | 9/2006 |
| WO | WO 2007084846 | 7/2007 |
| WO | WO 2009158522 | 12/2009 |
| WO | WO 2010099142 | 9/2010 |
| WO | WO 2011015863 | 2/2011 |
| WO | WO 2011063281 | 5/2011 |
| WO | WO 2011151657 | 12/2011 |
| WO | WO 2012088036 | 6/2012 |
| WO | WO 2012116089 | 8/2012 |
| WO | 2020124047 A1 | 6/2020 |

OTHER PUBLICATIONS

Extended European Search Report issued in connection with European U.S. Appl. No. 22/172,072, filed May 4, 2023, 25 pages.

Anonymous: Newtonian Telescope—Wikipedia, May 23, 2021, 6 pages.

Anonymous: "Light Tube—Wikipedia", Mar. 4, 2021, 11 pages.

Search report issued for European patent application No. 13198280 dated Feb. 5, 2014.

International Search Report for International patent application No. PCT/US2014/027448 dated Jul. 7, 2014.

International Preliminary Report on Patentability issued for International patent application No. PCT/US2014/027448, Sep. 15, 2015, 8 pages.

Partial European Search Report issued in connection with European patent application No. 14768333.8, Oct. 26, 2016, 6 pages.

Patent Examination Report No. 1 issued in connection with Australian patent application No. 2015202080, Jul. 5, 2016, 4 pages.

Office Action in corresponding Canadian Patent Application No. 2,904,652, Jun. 2, 2020, 6 pages.

First Examination Report issued in corresponding Australian Patent Application No. 2019213412, Sep. 3, 2020, 5 pages.

First Office Action in corresponding Canadian Patent Application No. 2,904,652, Jan. 28, 2020, 5 pages.

Final Office Action issued in connection with corresponding Japanese Patent Application No. 206-502443, May 15, 2018, 3 pages.

Extended European Search Report issued in connection with corresponding European Patent Application No. 18160378.8, Jun. 29, 2018, 7 pages.

Examination Report No. 1 issued in connection with corresponding Australian Patent Application No. 20182000073, Dec. 24, 2018, 3 pages.

Extended European Search Report and Opinion in connection with European Patent Application No. 14768333.8, dated Jan. 30, 2017, 10 pages.

Partial European Search Report issued in connection with Application No. 22172072.5, Jan. 23, 2023, 18 pages.

* cited by examiner

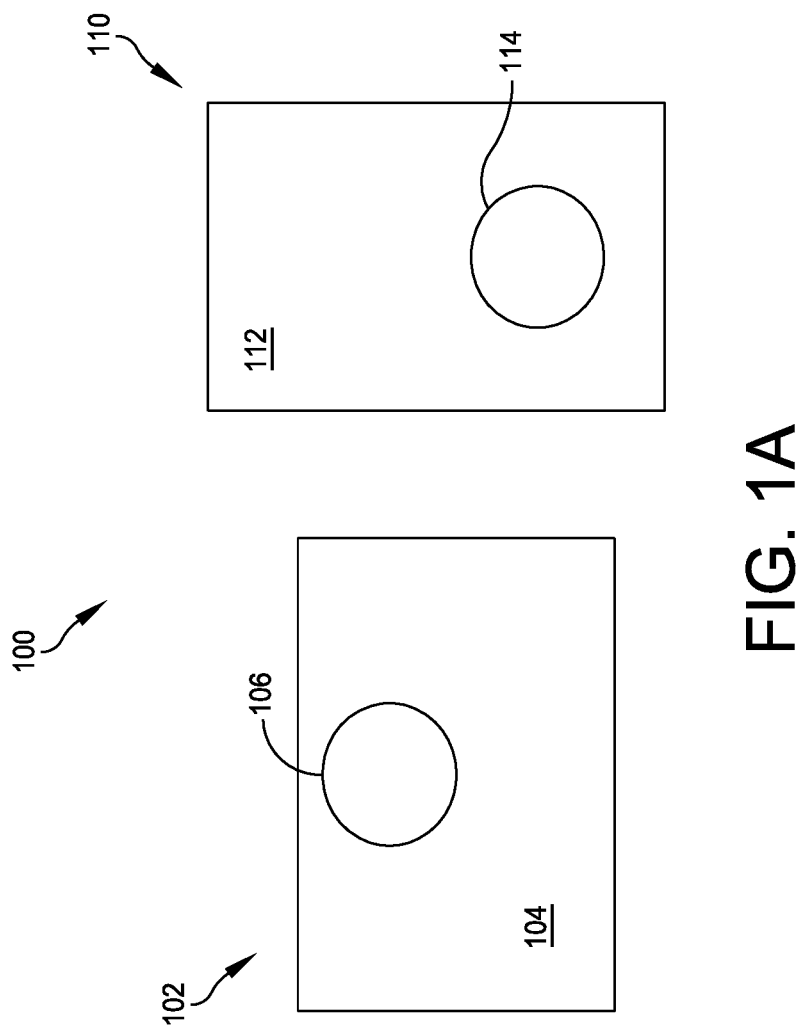

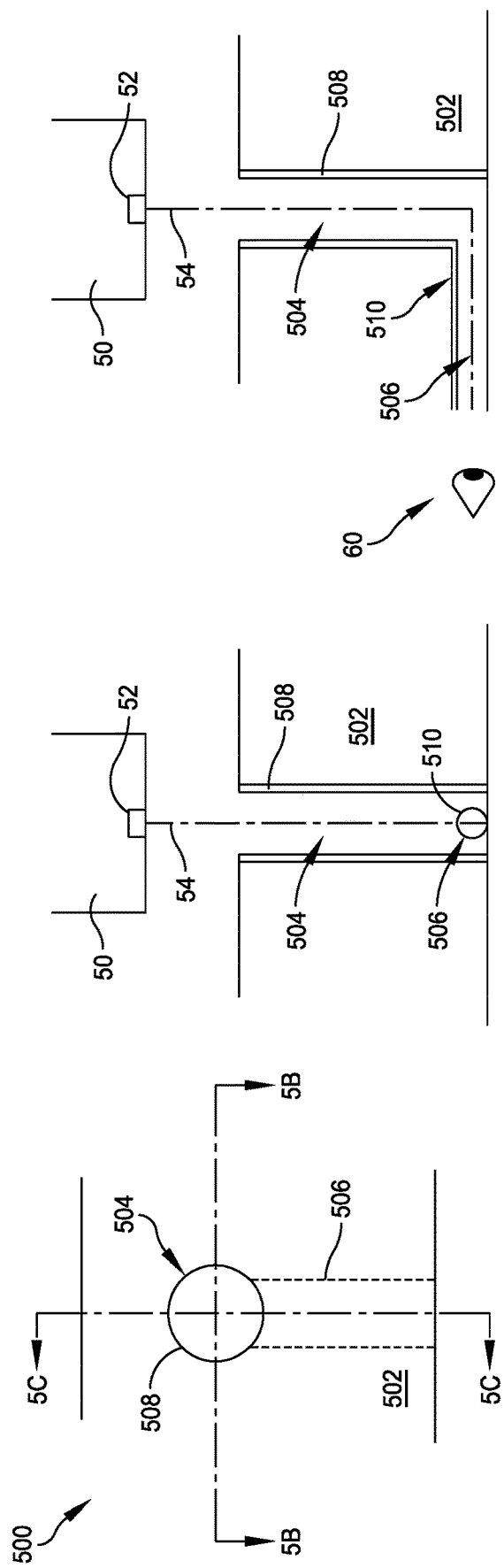

ALIGNMENT SYSTEMS AND METHODS

CROSS-REFERENCE TO RELATED APPLICATION

This application claims priority under 35 U.S.C. § 119(e) to U.S. Provisional Application No. 63/208,572, filed Jun. 9, 2021, the entirety of which is incorporated by reference herein.

FIELD OF DISCLOSURE

The disclosed systems and methods relate to the field of medical radiography. More particularly, the disclosed systems and methods relate to providing enhances visualization for ensuring that a prosthesis, fixture, and/or jig used in a surgical procedure is positioned properly.

BACKGROUND

Numerous surgical procedures use fluoroscopy to confirm a surgical plan and/or a placement of a surgical device, such as a fixture, prosthesis, and/or jig relative to a patient's anatomy. Ensuring proper alignment between a fluoroscopic device (e.g., an X-ray device supported by a C-arm) and an anatomical plane and/or surgical instrument is critical to ensuring that the information provided by fluoroscopy is accurate.

SUMMARY

In some embodiments, a system includes a first component and a second component. The first component has a first body supporting a first alignment member. The second component has a second body supporting a second alignment member. The first and second alignment members are separated from another and are configured to provide an indication that a fluoroscopic device is properly aligned with an anatomical plane when viewed under fluoroscopy.

In some embodiments, a method includes placing a first component supporting a first alignment member and a second component supporting a second alignment member relative to a patent, and aligning a fluoroscopic device with an anatomical plane using the first and second alignment members.

In some embodiments, a system includes an alignment device having a body defining a first aperture and a second aperture. The first and second apertures are disposed at an angle with one another. The first and second apertures are in communication with one another such that light passes through the first and second apertures when a fluoroscopic device is aligned with an anatomical plane.

In some embodiments, a method includes receiving light emitted from a light source in a first aperture defined by an alignment device, and directing the light from the first aperture defined by the alignment device to a second aperture defined by the alignment device such that light exits the alignment device from the second aperture. The second aperture is disposed at an angle with respect to the first aperture. The second aperture is disposed at an angle with respect to the first aperture.

In some embodiments, a system includes a first surgical device and an alignment adapted. The first surgical device is configured to be coupled to a patient. The alignment adapter has a body including a planar surface and a coupling mechanism for coupling the alignment adapter to the first surgical device such that the planar surface is parallel to an anatomical plane when the first surgical device is coupled to the patient and the alignment adapter is coupled to the first surgical device.

In some embodiments, a method includes placing a first surgical device relative to a patient, coupling an alignment device to the first surgical device, and aligning a fluoroscopic device with the planar surface of the alignment device. The alignment device includes a planar surface.

BRIEF DESCRIPTION OF THE DRAWINGS

The description of the exemplary embodiments disclosed herein are intended to be read in connection with the accompanying drawings, which are to be considered part of the entire written description. All drawing figures are schematic illustrations and are not intended to show actual dimensions or proportions.

FIG. 1A is a first side view of first and second components each having a respective alignment member in accordance with some embodiments;

FIG. 5A is a first side view of an alignment device in accordance with some embodiments;

FIG. 5B is a cross-sectional view of the alignment device illustrated in FIG. 5A taken along line 5B-5B in FIG. 5A positioned beneath a fluoroscopic device in accordance with some embodiments;

FIG. 5C is a cross-sectional view of the alignment device illustrated in FIG. 5A taken along line 5C-5C in FIG. 5A positioned beneath a fluoroscopic device in accordance with some embodiments.

DETAILED DESCRIPTION

Figure 1C:
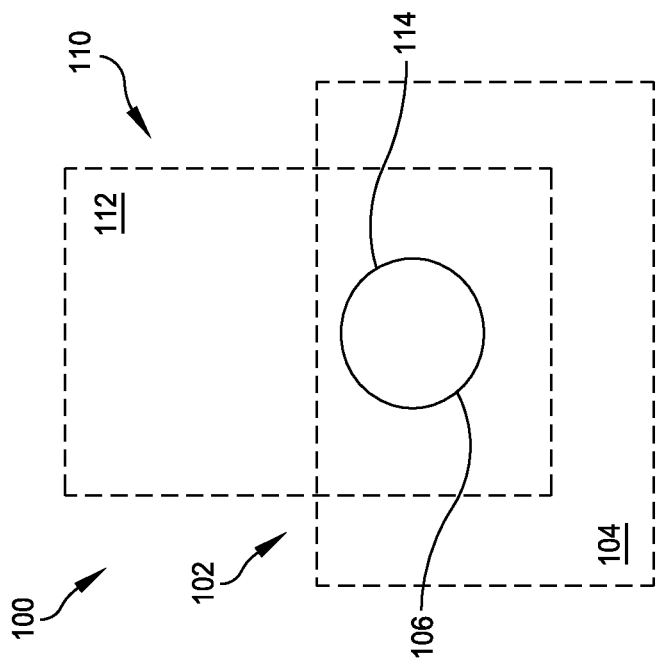
FIG. 1C is a representation of the first and second components illustrated in FIG. 1A being viewed under fluoroscopy when the fluoroscopic device is aligned properly with the first and second components in accordance with some embodiments.

This description of the exemplary embodiments is intended to be read in connection with the accompanying drawings, which are to be considered part of the entire written description. The drawing figures are not necessarily to scale, and certain features may be shown exaggerated in scale or in somewhat schematic form in the interest of clarity and conciseness. In the description, relative terms such as "horizontal," "vertical," "up," "down," "top" and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. When only a single machine is illustrated, the term "machine" shall also be taken to include any collection of machines that individually or jointly execute a set (or multiple sets) of instructions to perform any one or more of the methodologies discussed herein. The term "operatively connected" is such an attachment, coupling or connection that allows the pertinent structures to operate as intended by virtue of that relationship. In the claims, means-plus-function clauses, if used, are intended to cover the structures described, suggested, or rendered obvious by the written description or drawings for performing the recited function, including not only structural equivalents but also equivalent structures.

Fluoroscopy is commonly used during surgical procedures to ensure the proper alignment and/or orientation of prosthesis, fixture, and/or jig relative to a patient's anatomy. However, care must be taken to ensure that the fluoroscopic device (e.g., x-ray, C-arm) is properly aligned with the prosthesis, fixture, and/or jig.

FIG. 1A illustrates one example of a system 100 in accordance with some embodiments. In some embodiments, system 100 includes a first component 102 having a body 104 supporting a first alignment member 106. A second component 110 has a body 112 supporting a second alignment member 114. The bodies 104, 112 of the first and second components 102, 110 may be formed from a radiolucent material, including but not limited to polymers, PEEK, ABS, Nylon, etc., such that the bodies 104, 112 are invisible or only partially visible when viewed under fluoroscopy as will be understood by one of ordinary skill in the art. Although first and second components 102, 110 are shown as being separate components, it should be understood that the first and second components may be configured as first and second portions of a common device (e.g., the same prosthesis, fixture, and/or jig), but disposed at a distance from one another.

Further, although first and second components 102, 110 are described as each including a single alignment member, or parallax cues, i.e., alignment members 106, 114, first and second components 102, 110 may include plural alignment members, which may be oriented in the same or different planes. For example, first and second components 102, 110 may include one or more alignment members 106, 114 disposed in a first plane (e.g., coronal plane) and may also include one or more alignment members disposed in a second plane (e.g., sagittal or transverse plane). The alignment members may communicate position in 3D space while accounting for 2D fluoroscopy and inherent parallax in the image processing.

In some embodiments, the first and second alignment members 106, 114 are formed from a radiopaque material such that the first and second alignment members may be visualized under fluoroscopy. As seen in FIG. 1A, the first and second alignment members 106, 114 have the same shape and dimensions as one another for reasons discussed herein. Although the first and second alignment members 106, 114 are shown as having a circular or ring shape, it should be understood that the shape and size of the alignment members 106, 114 may vary. Further, the radiodensity (or radiopacity) of alignment members 106, 114 may be the same or different. Radiopaque materials may include metals, alloys, or other dense elements, such as titanium or tantalum.

The manner in which the first and second alignment members 106, 114 are supported by the first and second components 102, 110 also may vary. For example, the alignment members 106, 114 may be embedded within the respective bodies 104, 112 of the first and second components 102, 110. In some embodiments, the alignment members 106, 114 are affixed to a surface of the first and second components 102, 110, such as by using an adhesive or mechanical coupling. It should be understood that the first and second alignment members 106, 114 may be supported by the first and second components 102, 110 through different means. For example, the first alignment member 106 may be embedded within body 104 of first component 102, and second alignment member 114 may be affixed to a surface of body 112 of second component 110.

Figure 1B:
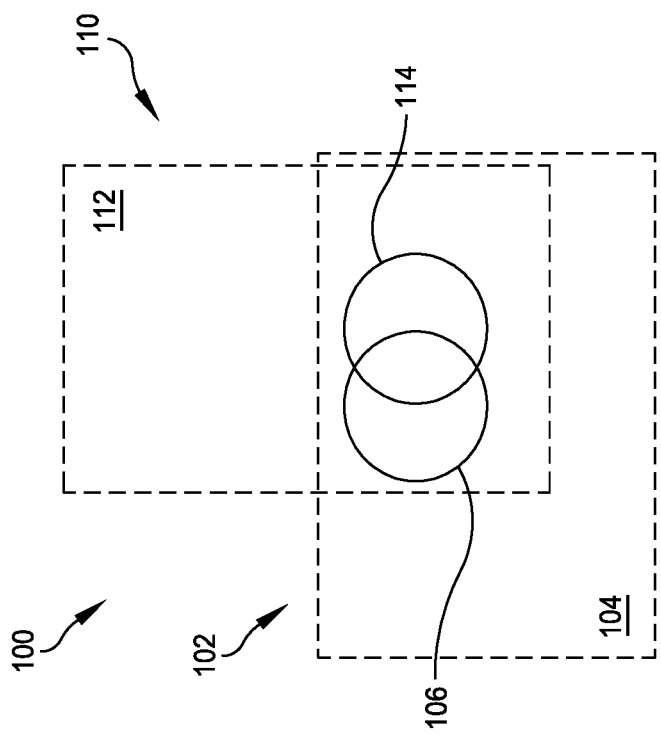
FIG. 1B is a representation of the first and second components illustrated in FIG. 1A being viewed under fluoroscopy when there is a misalignment between the fluoroscopic device and the first and second components in accordance with some embodiments.

FIG. 1B illustrates one example of the system 100 being viewed under fluoroscopy when there is a misalignment between the fluoroscopic device (e.g., X-ray and/or C-arm) and an anatomical plane, and FIG. 1C illustrates one example of the system 100 being view under fluoroscopy when the fluoroscopic device (e.g., X-ray and/or C-arm) are aligned properly with an anatomical plane. As is apparent through a comparison of FIGS. 1B and 1C, the misalignment is identifiable when both alignment members 106, 114 are visible under fluoroscopy (FIG. 1B) and the fluoroscopic device is properly aligned with the system when the two alignment members 106, 114 appear as one (FIG. 1C).

Figure 2A:
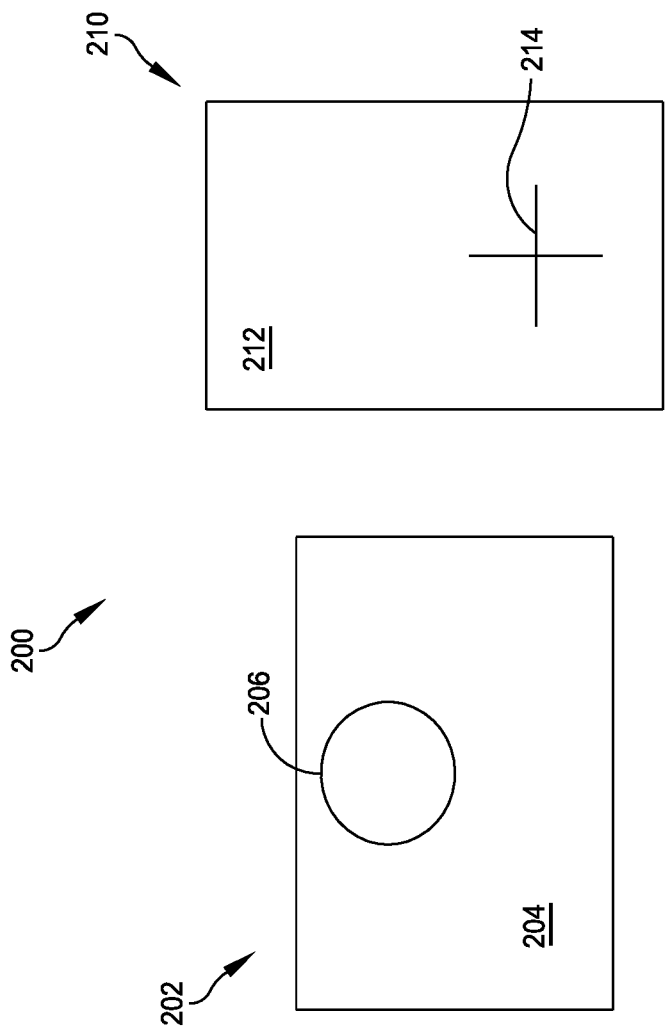
FIG. 2A is a first side view of another example of first and second components each having a respective alignment member in accordance with some embodiments.

FIG. 2A illustrates another example of a system in accordance with some embodiments. System 200 includes a first component 202 having a body 204 supporting a first alignment member 206. A second component 210 has a body 212 supporting a second alignment member 214. The bodies 204, 212 of the first and second components 202, 210 may be formed from a radiolucent material such that the bodies 204, 212 are invisible or only partially visible when viewed under fluoroscopy as will be understood by one of ordinary skill in the art. Although first and second components 202, 210 are shown as being separate components, it should be understood that the first and second components may be configured as first and second portions of a common device (e.g., the same prosthesis, fixture, and/or jig), but disposed at a distance from one another.

In some embodiments, the first and second alignment members 206, 214 are formed from a radiopaque material such that the first and second alignment members may be visualized under fluoroscopy. As seen in FIG. 2A, the first and second alignment members 206, 214 have different complementary shapes. More particularly, alignment member 206 is shown as being in the shape of a circle and alignment member 214 is shown as being in the shape of a crosshair that is dimensioned to correspond to the shape of alignment member 206. It should be understood that although alignment member 206 is illustrated as being a circle and alignment member 214 is illustrated as a crosshair, alignment members 206, 214 may have other shapes or configurations. For example, alignment member 206 may have another shape, such as a square, smaller ring, rectangle, triangle, etc., and/or alignment member 214 may take the form of a dot, circle, or other shape that is designed to provide an indication of alignment as will be understood by one of ordinary skill in the art. Further, the radiodensity (or radiopacity) of alignment members 206, 214 may be the same or different.

Although first and second components 202, 210 are described as each including a single alignment member, i.e., alignment members 206, 214, first and second components 202, 210 may include plural alignment members, which may be oriented in the same or different planes. For example, first and second components 202, 210 may include one or more alignment members 206, 214 disposed in a first plane (e.g., coronal plane) and may also include one or more alignment members disposed in a second plane (e.g., sagittal or transverse plane).

The manner in which the first and second alignment members 206, 214 are supported by the first and second components 202, 210 may also vary. For example, the alignment members 206, 214 may be embedded within the respective bodies 204, 212 of the first and second components 202, 210. In some embodiments, the alignment members 206, 214 are affixed to a surface of the first and second components 202, 210, such as by using an adhesive or mechanical coupling. It should be understood that the first and second alignment members 206, 214 may be supported by the first and second components 202, 210 through different means. For example, the first alignment member 206 may be embedded within body 204 of first component 202, and second alignment member 214 may be affixed to a surface of body 212 of second component 210.

Figure 2C:
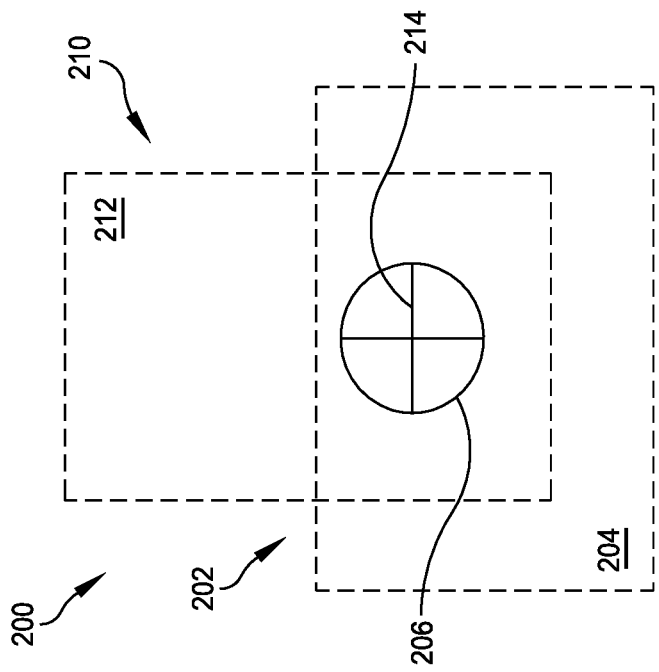
FIG. 2C is a representation of the first and second components illustrated in FIG. 2A being viewed under fluoroscopy when the fluoroscopic device is aligned properly with the first and second components in accordance with some embodiments.
Figure 2B:
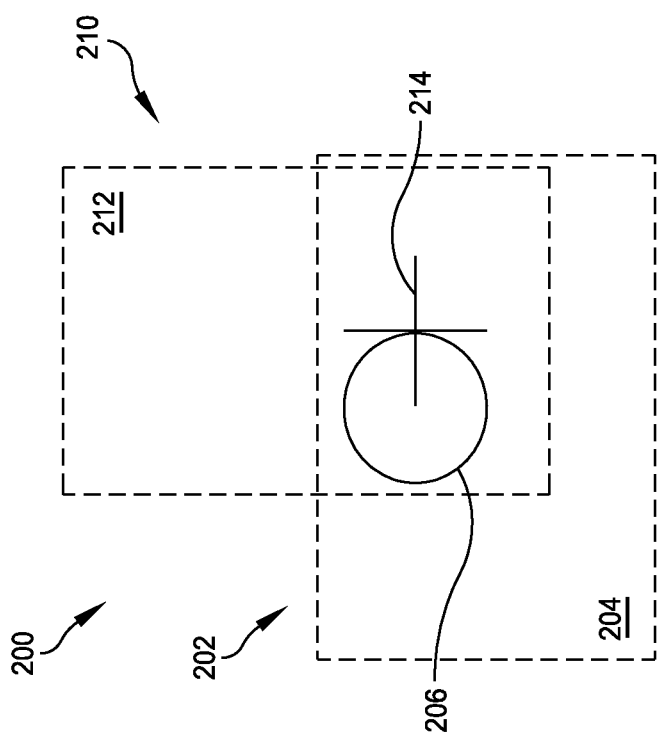
FIG. 2B is a representation of the first and second components illustrated in FIG. 2A being viewed under fluoroscopy when there is a misalignment between the fluoroscopic device and the first and second components in accordance with some embodiments.

FIG. 2B illustrates one example of the system 200 being viewed under fluoroscopy when there is a misalignment between the fluoroscopic device (e.g., X-ray and/or C-arm) and an anatomic plane, and FIG. 2C illustrates one example of the system 200 being view under fluoroscopy when the fluoroscopic device (e.g., X-ray, imaging device, and/or C-arm) is aligned properly with an anatomical plane. As is apparent through a comparison of FIGS. 2B and 2C, the misalignment is identifiable when alignment member 214 is not positioned properly with respect to alignment member 206, i.e., crosshair is not disposed within and encircled by the circle (FIG. 2B), and the fluoroscopic device is aligned properly with system 200 when alignment member 214 is disposed within and encircled by alignment member 206 (FIG. 2C).

Figure 3A:
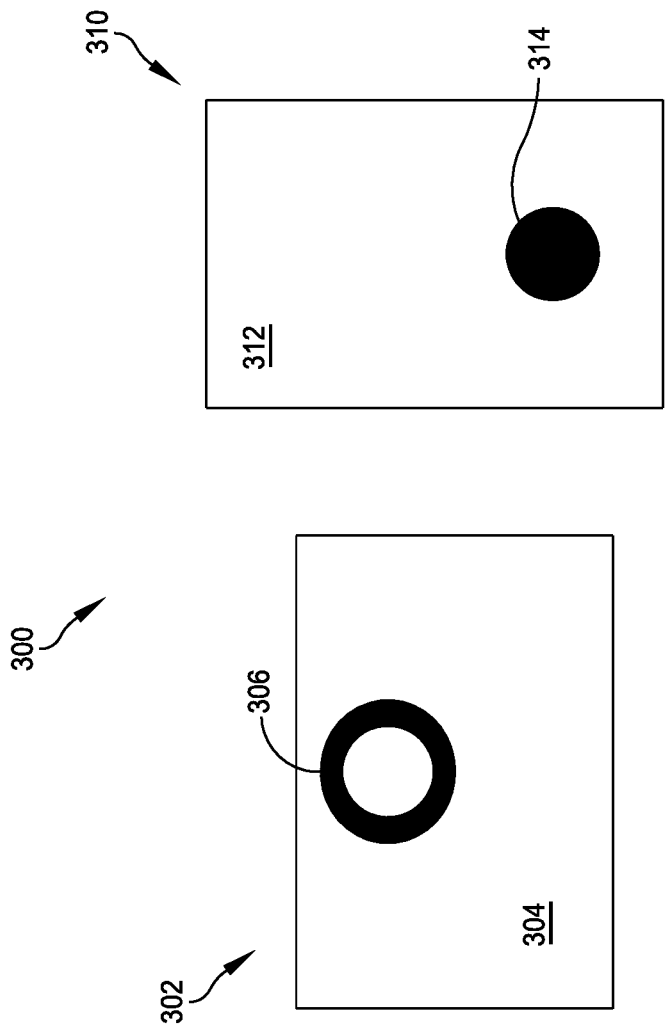
FIG. 3A is a first side view of another example of first and second components each having a respective alignment member in accordance with some embodiments.

FIG. 3A illustrates another example of a system in accordance with some embodiments. System 300 includes a first component 302 having a body 304 supporting a first alignment member 306. A second component 310 has a body 312 supporting a second alignment member 314. The bodies 304, 312 of the first and second components 302, 310 may be formed from a radiolucent material such that the bodies 304, 312 are invisible or only partially visible when viewed under fluoroscopy as will be understood by one of ordinary skill in the art. Although first and second components 302, 310 are shown as being separate components, it should be understood that the first and second components may be configured as first and second portions of a common device (e.g., the same prosthesis, fixture, and/or jig), but disposed at a distance from one another.

In some embodiments, the first and second alignment members 306, 314 are formed from a radiopaque material such that the first and second alignment members may be visualized under fluoroscopy. As seen in FIG. 3A, the first and second alignment members 306, 314 have different complementary shapes. More particularly, alignment member 306 is shown as being in the shape of a circle and alignment member 314 is shown as being a dot that is sized and configured to fill the entirety of the circle of alignment member 306. In some embodiments, the radiodensity (or radiopacity) of alignment members 306, 314 may be the same or different.

Further, although first and second components 302, 310 are described as each including a single alignment member, i.e., alignment members 306, 314, first and second components 302, 310 may include plural alignment members, which may be oriented in the same or different planes. For example, first and second components 302, 310 may include one or more alignment members 306, 314 disposed in a first plane (e.g., coronal plane) and may also include one or more alignment members disposed in a second plane (e.g., sagittal or transverse plane).

The manner in which the first and second alignment members 306, 314 are supported by the first and second components 302, 310 also may vary. For example, the alignment members 306, 314 may be embedded within the respective bodies 304, 312 of the first and second components 302, 210. In some embodiments, the alignment members 306, 314 are affixed to a surface of the first and second components 302, 310, such as by using an adhesive or mechanical coupling. It should be understood that the first and second alignment members 306, 314 may be supported by the first and second components 302, 310 through different means. For example, the first alignment member 306 may be embedded within body 304 of first component 302, and second alignment member 314 may be affixed to a surface of body 312 of second component 310.

Figure 3C:
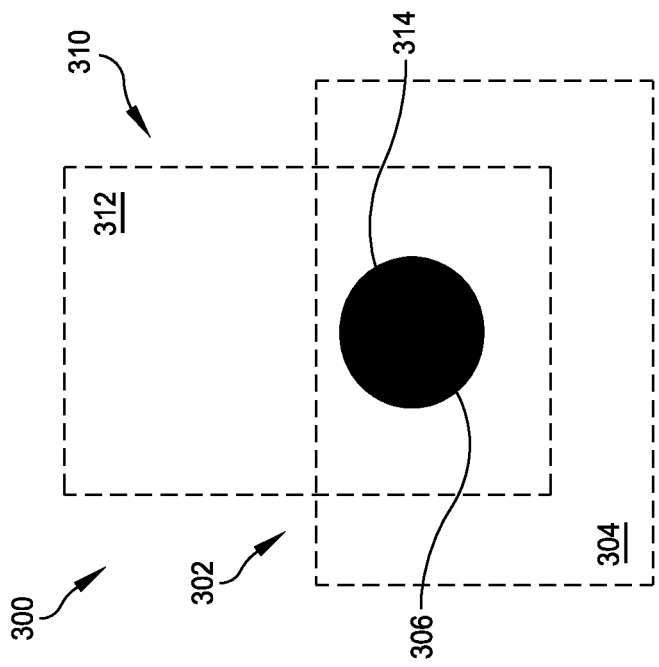
FIG. 3C is a representation of the first and second components illustrated in FIG. 3A being viewed under fluoroscopy when the fluoroscopic device is aligned properly with the first and second components in accordance with some embodiments.
Figure 3B:
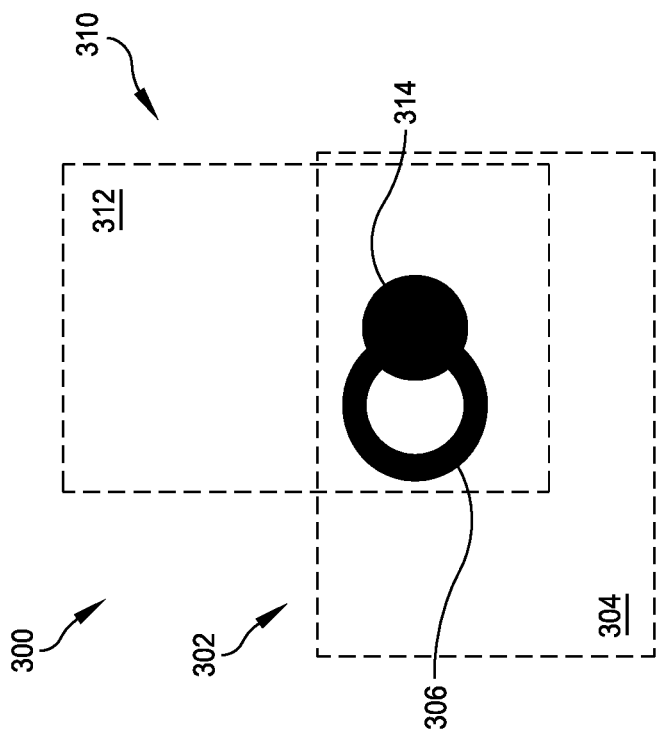
FIG. 3B is a representation of the first and second components illustrated in FIG. 3A being viewed under fluoroscopy when there is a misalignment between the fluoroscopic device and the first and second components in accordance with some embodiments.

FIG. 3B illustrates one example of the system 300 being viewed under fluoroscopy when there is a misalignment between the fluoroscopic device (e.g., X-ray and/or C-arm) and an anatomical plane, and FIG. 3C illustrates one example of the system 300 being view under fluoroscopy when the fluoroscopic device (e.g., X-ray, imaging device, and/or C-arm) aligned properly with an anatomical plane. As is apparent through a comparison of FIGS. 3B and 3C, the misalignment is identifiable when alignment member 314 is not positioned properly with respect to alignment member 306, i.e., dot is not disposed within and fill the circle (FIG. 3B), and the fluoroscopic device is aligned properly with system 300 when alignment member 314 is disposed within and fills alignment member 306 (FIG. 3C).

Figure 4:
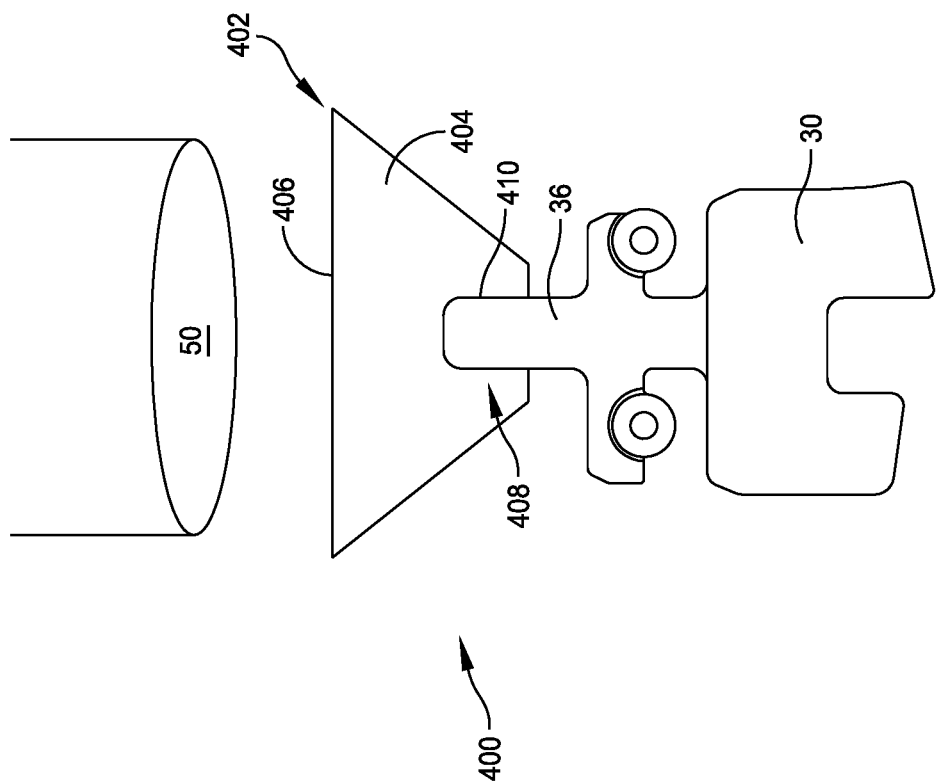
FIG. 4 is a side view of one example of an alignment adapter in accordance with some embodiments.

FIG. 4 illustrates another example of a system in accordance with some embodiments. More particularly, the alignment system provided in FIG. 4 includes an alignment adapter 402 that is sized and configured to engage another surgical device 30, such as the alignment guide 30 disclosed in U.S. Pat. No. 9,402,640, entitled "Alignment Guide with Embedded Features for Intra-Operative Fluoro-Checks," which is incorporated by reference herein in its entirety.

Adapter 402 includes a body 404 that includes an enlarged planar surface 406 and a coupling mechanism 408. In some embodiments, planar surface 406 is enlarged with respect to the rest of the body 404 and provides for enhanced visualization such that the alignment between the surgical device 30 and the fluoroscopic device 50 may be checked or confirmed as described below. Coupling mechanism 408 may take a variety of forms to facilitate the coupling of adapter 402 to surgical device 30. For example and as depicted in FIG. 4, coupling mechanism 408 may the take the form of a channel 410 that is sized and configured to receive and/or engage at least a portion (e.g., the anterior protruding portion 36) of surgical device 30. It should be understood that the size and nature of coupling mechanism 408 may vary based on the characteristics of the device 30. Examples of other coupling mechanisms include, but are not limited to, a slot with dovetail connection, a detent, a hole for receiving a pin, and a protrusion designed to be inserted into a slot or hole defined by device 30, to list only a few possible examples.

Coupling mechanism 408 is designed to engage device 30 such that planar surface 406 is oriented relative to device 30 in a predetermined manner. For example, in some embodiments, coupling mechanism 408 is sized and configured to engage device 30 such that planar surface is parallel to a longitudinal axis of a radiopaque member (e.g., radiopaque members 34a, 34b, 35 disclosed in U.S. Pat. No. 9,402,640) supported by device 30.

With adapter 402 coupled to device 30, a surgeon, radiographic technician, or other individual may align the fluoroscopic device 50 with device 30 by visually determining whether the planar surface 406 of adapter 302 is oriented parallel to fluoroscopic device 50. The enlarged surface 406 provided by adapter 402 is easier to align with fluoroscopic device 50 compared to a surface feature of device 30. In some embodiments, adapter 402 and surgical device 30 may include cooperative alignment members, such as the alignment members described above with reference to FIGS. 1A-1C, 2A-2C, and 3A-3C.

FIGS. 5A-5C illustrates another example of an alignment device 500 in accordance with some embodiments. More particularly, FIG. 5A is a top side view of one example of an alignment device 500, FIG. 5B is a cross-sectional view of the device 500 taken along line 5B-5B in FIG. 5A, and FIG. 5C is a cross-sectional view of the device 500 taken along line 5C-5C in FIG. A.

Alignment device 500 has a body 502 that may be formed from a radiolucent material. In some embodiments, body 502 defines first and second apertures 504, 506 that are oriented at an angle with respect to one another. For example, apertures 504, 506 may be orthogonally oriented relative to one another such that aperture 504 is disposed parallel to a first plane (e.g., coronal, medial, sagittal, or transverse plane) and aperture 506 is disposed parallel to a second plane that is different from the first plane (e.g., another of the coronal, medial, sagittal, and transverse planes). However, it should be understood that apertures 504, 506 may be disposed at other angles (e.g., oblique or obtuse angles) relative to one another. As best seen in FIGS. 5B and 5C, apertures 504, 506 intersect one another within body 502.

In some embodiments, liners 508, 510 are disposed within apertures 504, 506, respectively. Liners 506, 508 may be formed from a reflective material and be configured to direct light 54, which is provided by a laser, light emitting diode (LED), or illuminating device 52, along their lengths. In some embodiments, the illuminating device 52 is supported by or coupled to an fluoroscopic device 50, which may be supported by or include a C-arm as will be understood by one of ordinary skill in the art.

In use, alignment device 500 is positioned either one a patient or coupled to another surgical instrument, such as a prosthetic, fixture, and/or jig. An illuminating device or light source 52, which is coupled to or provided by a C-arm and/or fluoroscopic device 50, directs light 54 into one of the apertures (e.g., aperture 504 as shown in FIGS. 5A-5C). When the fluoroscopic device is properly aligned with the device 500, the light 54 is received within aperture 504 (and liner 508, if provided) and is visible to the surgeon via aperture 506 (and liner 510, if provided). As noted above, the liners 508, 510 may reflect the light along their lengths to enable the light to be viewed by the surgeon, technician, or other individual 60 (FIG. 5C) and prevents the device 500 from being illuminated entirely by illuminating device 52.

Figure 5D:
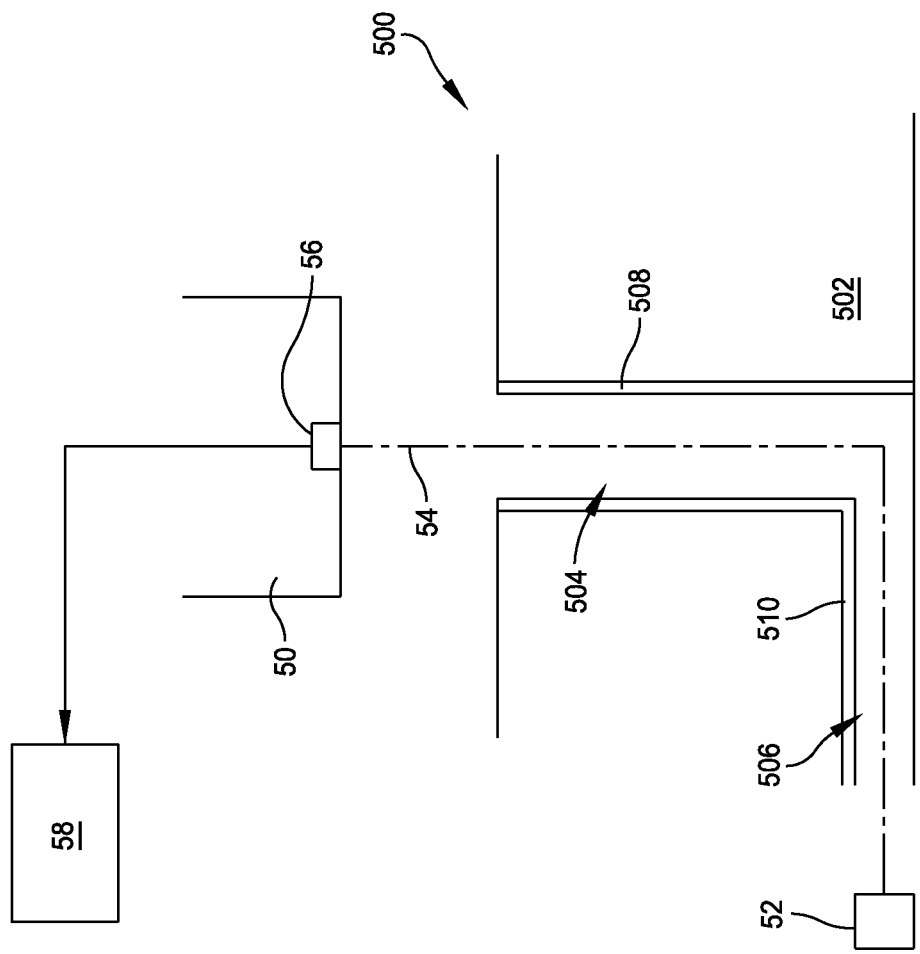
FIG. 5D is a cross-sectional view of the alignment device illustrated in FIG. 5A taken along line 5C-5C in FIG. 5A in use with another system in accordance with some embodiments.

FIG. 5D illustrates another system in which alignment device 500 may be included. As shown in FIG. 5D, a light source 52 directs light into aperture 506 (and liner 510, if provided) and a camera or optical sensor 56 is provided on the fluoroscopic device 50 (e.g., X-ray lens, C-arm, etc.) to detect light exiting aperture 504 (guided by liner 508, if provided). In some embodiments, the camera 56 is coupled to a control and image processing system 58, which may be configured to detect the light emanating from aperture 504 and move the C-arm and fluoroscopic device into position based on the light detected by camera or optical sensor 56. One example of a control and image processing system is imaging system 200 disclosed in U.S. Pat. No. 8,611,697, which is incorporated by reference herein in its entirety.

In some embodiments, a system includes a first component and a second component. The first component has a first body supporting a first alignment member. The second component has a second body supporting a second alignment member. The first and second alignment members are separated from another and are configured to provide an indication that a fluoroscopic device is properly aligned with an anatomical plane when viewed under fluoroscopy.

In some embodiments, the first component and the second component are respective portions of a common device.

In some embodiments, a shape of the first alignment member is the same as a shape of the second alignment member.

In some embodiments, a dimension of the first alignment member is the same as a dimension of the second alignment member.

In some embodiments, a radiopacity of the first alignment member is different from a radiopacity of the second alignment member.

In some embodiments, a shape of the first alignment member is different from a shape of the second alignment member.

In some embodiments, the shape of the first alignment member is complementary to the shape of the second alignment member.

In some embodiments, the shape of the first alignment member is circular.

In some embodiments, the second alignment member includes a crosshair.

In some embodiments, the shape of the second alignment member is a dot sized to fill an opening of the circular shape of the first alignment member.

In some embodiments, a method includes placing a first component supporting a first alignment member and a second component supporting a second alignment member relative to a patent, and aligning a fluoroscopic device with an anatomical plane using the first and second alignment members.

In some embodiments, aligning the fluoroscopic device with the anatomical plane includes viewing the first and second alignment members under fluoroscopy.

In some embodiments, the first and second alignment members appear as a single alignment member when the fluoroscopic device is aligned with the anatomical plane.

In some embodiments, the first and second alignment members have a complementary shape when the fluoroscopic device is aligned with the anatomical plane.

In some embodiments, a system includes an alignment device having a body defining a first aperture and a second aperture. The first and second apertures are disposed at an angle with one another. The first and second apertures are in communication with one another such that light passes through the first and second apertures when a fluoroscopic device is aligned with an anatomical plane.

In some embodiments, a first liner is disposed within the first aperture. The first liner is configured to direct light along a length of the first aperture.

In some embodiments, a second liner is disposed within the second aperture. The second liner is configured to direct light along a length of the second aperture.

In some embodiments, a system includes a light source configured to direct light into at least one of the first aperture and the second aperture.

In some embodiments, the light source is coupled to a C-arm of a radiographic device.

In some embodiments, a system includes an optical sensor coupled to a C-arm of a radiographic device. The optical detector is configured to detect light exiting at least one of the first aperture and the second aperture.

In some embodiments, a system includes a camera coupled to a C-arm of a radiographic device. The camera is configured to receive light from at least one of the first aperture and the second aperture.

In some embodiments, a method includes receiving light emitted from a light source in a first aperture defined by an alignment device, and directing the light from the first aperture defined by the alignment device to a second aperture defined by the alignment device such that light exits the alignment device from the second aperture. The second aperture is disposed at an angle with respect to the first aperture. The second aperture is disposed at an angle with respect to the first aperture.

In some embodiments, the light emitted from the light source is received within the first aperture when a fluoroscopic device is aligned with an anatomical axis.

In some embodiments, a method includes detecting light exiting the alignment device using an optical sensor.

In some embodiments, a method includes adjusting a position of a fluoroscopic device if light is not detected by the optical sensor.

In some embodiments, a method includes detecting light exiting the alignment device using a camera.

In some embodiments, a method includes adjusting a position of a fluoroscopic device if light is not detected by the camera.

In some embodiments, a system includes a first surgical device and an alignment adapted. The first surgical device is configured to be coupled to a patient. The alignment adapter has a body including a planar surface and a coupling mechanism for coupling the alignment adapter to the first surgical device such that the planar surface is parallel to an anatomical plane when the first surgical device is coupled to the patient and the alignment adapter is coupled to the first surgical device.

In some embodiments, the coupling mechanism includes a channel sized and configured to receive at least a portion of the first surgical device.

In some embodiments, the coupling mechanism includes a detent sized and configured to engage the first surgical device.

In some embodiments, the coupling mechanism includes a slot having a dovetail that is sized and configured to engage a corresponding feature of the first surgical device.

In some embodiments, a method includes placing a first surgical device relative to a patient, coupling an alignment device to the first surgical device, and aligning a fluoroscopic device with the planar surface of the alignment device. The alignment device includes a planar surface.

In some embodiments, a method includes adjusting a position of the fluoroscopic device until the fluoroscopic device is aligned with the planar surface of the alignment device.

In some embodiments, the planar surface of the alignment device is parallel to an anatomical plane of the patient.

Although the systems and methods have been described in terms of exemplary embodiments, they are not limited thereto. Rather, the appended claims should be construed broadly, to include other variants and embodiments of the systems and methods, which may be made by those skilled in the art without departing from the scope and range of equivalents.

What is claimed is:

1. A system comprising:
   a first component having a first body supporting two or more first alignment members; and
   a second component having a second body supporting two or more second alignment members,
   wherein a first one of the two or more first alignment members and a first one of the two or more second alignment members are disposed in a first plane, and a second one of the two or more first alignment members and a second one of the two or more second alignment members are disposed in a second plane,
   wherein each of the two or more first alignment members are separated from each of the two or more second alignment members, and
   wherein the two or more first alignment members and the two or more second alignment members are configured to provide an indication that a fluoroscopic device is properly aligned with an anatomical plane and communicate position in 3D space when viewed under fluoroscopy.

2. The system of claim 1, wherein the first component and the second component are respective portions of a common device.

3. The system of claim 1, wherein a shape of the two or more first alignment members is the same as a shape of the two or more second alignment members.

4. The system of claim 3, wherein a dimension of the two or more first alignment members is the same as a dimension of the two or more second alignment members.

5. The system of claim 3, wherein a radiopacity of the two or more first alignment members is different from a radiopacity of the two or more second alignment members.

6. The system of claim 1, wherein a shape of the two or more first alignment members is different from a shape of the two or more second alignment members.

7. The system of claim 6, wherein the shapes of the two or more first alignment members are complementary to the shapes of the two or more second alignment members.

8. The system of claim 7, wherein the shapes of the two or more first alignment members are circular.

9. The system of claim 8, wherein the two or more second alignment members each comprise a crosshair.

10. The system of claim 8, wherein the shapes of the two or more second alignment members are a dot sized to fill an opening of the circular shapes of the two or more first alignment members.

11. A method, comprising:
placing a first component supporting two or more first alignment members and a second component supporting two or more second alignment members relative to a patient,
wherein a first one of the two or more first alignment members and a first one of the two or more second alignment members are disposed in a first plane, and a second one of the two or more first alignment members and a second one of the two or more second alignment members are disposed in a second plane to communicate position in 3D space when viewed under fluoroscopy, and
wherein each of the two or more first alignment members are separated from each of the two or more second alignment members; and
aligning a fluoroscopic device with an anatomical plane using the two or more first alignment members and the two or more second alignment members.

12. The method of claim 11, wherein aligning the fluoroscopic device with the anatomical plane includes viewing the two or more first alignment members and the two or more second alignment members under fluoroscopy.

13. The method of claim 12, wherein the first one of the two or more first and the first one of the two or more second alignment members disposed in the first plane appear as a single alignment member when the fluoroscopic device is aligned with the anatomical plane.

14. The method of claim 12, wherein the two or more first alignment members and the two or more second alignment members have a complementary shape when the fluoroscopic device is aligned with the anatomical plane.

15. A system, comprising:
an alignment device having a body defining a first aperture and a second aperture, the first and second apertures being disposed at an angle with one another; and
a fluoroscopic device spaced apart from the alignment device,
wherein the first and second apertures are in communication with one another such that light passes through the first and second apertures when the fluoroscopic device is aligned with the alignment device disposed in an anatomical plane, and
wherein the alignment device is configured to be positioned on a patient or coupled to a surgical instrument.

16. The system of claim 15, wherein a first liner is disposed within the first aperture, the first liner configured to direct light along a length of the first aperture.

17. The system of claim 16, wherein a second liner is disposed within the second aperture, the second liner configured to direct light along a length of the second aperture.

18. The system of claim 17, further comprising a light source configured to direct light into at least one of the first aperture and the second aperture.

19. The system of claim 18, wherein the light source is coupled to a C-arm of a radiographic device.

20. The system of claim 18, further comprising an optical sensor coupled to a C-arm of a radiographic device, the optical sensor configured to detect light exiting at least one of the first aperture and the second aperture.

21. The system of claim 18, further comprising a camera coupled to a C-arm of a radiographic device, the camera configured to receive light from at least one of the first aperture and the second aperture.

22. A method, comprising:
receiving light emitted from a light source in a first aperture defined by an alignment device positioned on a patient or coupled to a surgical instrument, the light source being spaced apart from the first aperture; and
directing the light from the first aperture defined by the alignment device to a second aperture defined by the alignment device such that light exits the alignment device from the second aperture, the second aperture disposed at an angle with respect to the first aperture,
wherein the directed light that exits the alignment device from the second aperture confirms alignment of the light source and the alignment device.

23. The method of claim 22, wherein the light emitted from the light source is received within the first aperture when a fluoroscopic device is aligned with an anatomical axis.

24. The method of claim 22, further comprising detecting light exiting the alignment device using an optical sensor.

25. The method of claim 24, further comprising adjusting a position of a fluoroscopic device if light is not detected by the optical sensor.

26. The method of claim 22, further comprising detecting light exiting the alignment device using a camera.

27. The method of claim 26, further comprising adjusting a position of a fluoroscopic device if light is not detected by the camera.

28. A system, comprising:
a first surgical device configured to be coupled to a patient, the first surgical device supporting one or more first alignment members; and
an alignment adapter having a body, the body including:
a planar surface,
a coupling mechanism for coupling the alignment adapter to the first surgical device such that the planar surface is parallel to an anatomical plane when the first surgical device is coupled to the patient and the alignment adapter is coupled to the first surgical device, and
one or more second alignment members,
wherein the one or more first alignment members and the one or more second alignment members are configured to provide an indication that a fluoroscopic device is properly aligned with an anatomical plane when viewed under fluoroscopy.

29. The system of claim 28, wherein the coupling mechanism includes a channel sized and configured to receive at least a portion of the first surgical device.

30. The system of claim 28, wherein the coupling mechanism includes a detent sized and configured to engage the first surgical device.

31. The system of claim 28, wherein the coupling mechanism includes a slot having a dovetail that is sized and configured to engage a corresponding feature of the first surgical device.

32. A method, comprising:
- placing a first surgical device relative to a patient, the first surgical device supporting one or more first alignment members;
- coupling an alignment device to the first surgical device, the alignment device including a planar surface and supporting one or more second alignment members; and
- aligning a fluoroscopic device with the planar surface of the alignment device, such that alignment of the one or more first alignment members and the one or more second alignment members provides an indication that the fluoroscopic device is properly aligned with an anatomical plane of a patient when viewed under fluoroscopy.

33. The method of claim 32, further comprising adjusting a position of the fluoroscopic device until the fluoroscopic device is aligned with the planar surface of the alignment device.

34. The method of claim 32, wherein the planar surface of the alignment device is parallel to an anatomical plane of the patient.

* * * * *